(12) United States Patent
Yu

(10) Patent No.: US 7,593,762 B2
(45) Date of Patent: Sep. 22, 2009

(54) SYSTEM AND METHOD FOR AUTOMATICALLY SEGMENTING BONES IN COMPUTED TOMOGRAPHY ANGIOGRAPHY DATA

(75) Inventor: Daphne Yu, Yardley, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 899 days.

(21) Appl. No.: 10/915,499

(22) Filed: Aug. 9, 2004

(65) Prior Publication Data

US 2005/0228272 A1    Oct. 13, 2005

Related U.S. Application Data

(60) Provisional application No. 60/561,187, filed on Apr. 9, 2004.

(51) Int. Cl.
*A61B 5/05*    (2006.01)
(52) U.S. Cl. .................. 600/425; 600/407; 382/131
(58) Field of Classification Search ............ 382/128, 382/131; 600/407, 425
See application file for complete search history.

(56) References Cited

U.S. PATENT DOCUMENTS

| | | | | |
|---|---|---|---|---|
| 4,590,558 | A * | 5/1986 | Glover et al. ................. | 378/6 |
| 5,832,134 | A * | 11/1998 | Avinash et al. ............... | 382/257 |
| 5,924,987 | A * | 7/1999 | Meaney et al. ............... | 600/420 |
| 6,690,816 | B2 * | 2/2004 | Aylward et al. .............. | 382/128 |
| 6,744,911 | B1 * | 6/2004 | Avila et al. ................... | 382/131 |
| 7,327,880 | B2 * | 2/2008 | Tek ............................. | 382/173 |
| 2005/0240094 | A1 * | 10/2005 | Pichon et al. ................ | 600/407 |

OTHER PUBLICATIONS

Giess et al. "Medical Image Processing and Visualization on Heterogenous Clusters of Symmetric Multiprocessors using MPI and POSIX Threads", IEEE Computer Society, 12th. International Parallel Processing Symposium, 1998, pp. 233-237.*
M. Alyassin et al., "Semi-Automatic Bone Removal Technique from CT Angiography Data", Proc. SPIE, Medical Imaging 2001, vol. 4322, 1273-1283.
T. Blaffert et al., "Bone Suppression in CT Angiography Data by Region-Based Multi-Resolution Segmentation", Proc. SPIE Medical Imaging 2003, vol. 5032, 527-534.
M. Straka et al., "Bone Segmentation in CT-Angiography Data Using a Probabilistic Atlas", Proceedings of Vision Modeling and Visualization, pp. 505-512, 2003.

* cited by examiner

*Primary Examiner*—Charles Kim
*Assistant Examiner*—Stephen R Koziol

(57) ABSTRACT

A system and method for automatically segmenting bone regions from Computed Tomography Angiography (CTA) volume data is disclosed. A locally operated bone detector distinguishes between bone regions and contrast agent filled vessels. A filtering operator removes small noise from the detected bone regions. A dilator expands the filtered detected bone regions to adjacent trabecular bones. A processor applies the dilated detected bone regions to the CTA volume data. A display shows the applied CTA volume data.

12 Claims, 5 Drawing Sheets

SYSTEM AND METHOD FOR AUTOMATICALLY SEGMENTING BONES IN COMPUTED TOMOGRAPHY ANGIOGRAPHY DATA

CROSS REFERENCE TO RELATED APPLICATION

This application claims the benefit of U.S. Provisional Application Ser. No. 60/561,187, filed on Apr. 9, 2004, which is incorporated by reference in its entirety.

FIELD OF THE INVENTION

The present invention is directed to a system and method for automatically segmenting bones in computed tomography angiography data, and more particularly, to a system and method for automatic bone mask extraction from computed tomography angiography data based on efficient feature detection and filtering methods.

BACKGROUND OF THE INVENTION

Visualization and analysis of large three dimensional (3D) Computed Tomography Angiography (CTA) image data has become a conventional practice. The visualization of data is commonly achieved by a maximum intensity projection or by volume rendering. However, due to the overlapping intensity distribution between bone and contrast enhanced vessels in CTA data, bone structures can be a major obstacle in the visualization and analysis of vessel trees, aneurisms and calcifications.

In the past, manual editing techniques have been used to extract and remove bone structures from the data. However, the tedious and long operating time required for the manual editing is prohibitive for it to be of practical use. This is particularly true as the size of the acquired data increases. For example, 3D images of the abdomen and legs are acquired today in 1000-2000 traverse images with 512×512 12-bit pixels for analysis of peripheral arterial occlusion diseases.

Semi-automatic methods exist for segmenting bone structures from a focused region of the body; however, these methods are often inefficient for use with large data, or are not sufficiently robust for extension to automatic clinical use cases. For example, methods that are crucially based on specific industry threshold constraints are generally not robust foundations for segmentation due to the variability of intensities in the different organ parts of a large image and in different data. Region growing based and other more elaborate graph based methods also pose problems for speed and memory consumption efficiency due to either incoherent data memory access or large memory consumption. These approaches are usually used for data capturing only a small region of the body, or for subsampled, lower resolution, versions of the original data.

Region growing based methods that rely only on region connectivity and simple constraints such as threshold ranges, also often face challenges when bones and vessels with overlapping intensity distribution also appear to be connected due to image resolution and noise in the data, which is a common case in routine clinical data. Other known methods had tried to improve the robustness by incorporating a priori knowledge. However, even when an anatomical atlas is available as the basis of a priori knowledge, the method still requires lengthy registration and sometimes manual interventions that are still not yet practical for routine use.

SUMMARY OF THE INVENTION

The present invention is directed to a system and method for automatically segmenting bone regions from Computed Tomography Angiography (CTA) volume data is disclosed. A locally operated bone detector distinguishes between bone regions and contrast agent filled vessels. A filtering operator removes small noise from the detected bone regions. A dilator expands the filtered detected bone regions to adjacent trabecular bones. A processor applies the dilated detected bone regions to the CTA volume data. A display shows the applied CTA volume data.

The present invention is also directed to a semi-automatic for segmenting bone regions from Computed Tomography Angiography (CTA) volume data. Grayscale CTA volume data for a patient is received. The CTA volume data contains bone regions and contrast agent filled vessels. A seed point is selected on the bone region. Neighboring voxels of the seed point in the CTA volume data are added to a queue to be processed by a locally operated bone detector. This process is repeated with additional neighboring voxels in the queue until there are no more neighboring voxels. The result is the detected bone mask. Noise is filtered from the bone mask. The bone mask is dilated. The bone mask is applied to the grayscale CTA volume data and displayed.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

Figure 1:
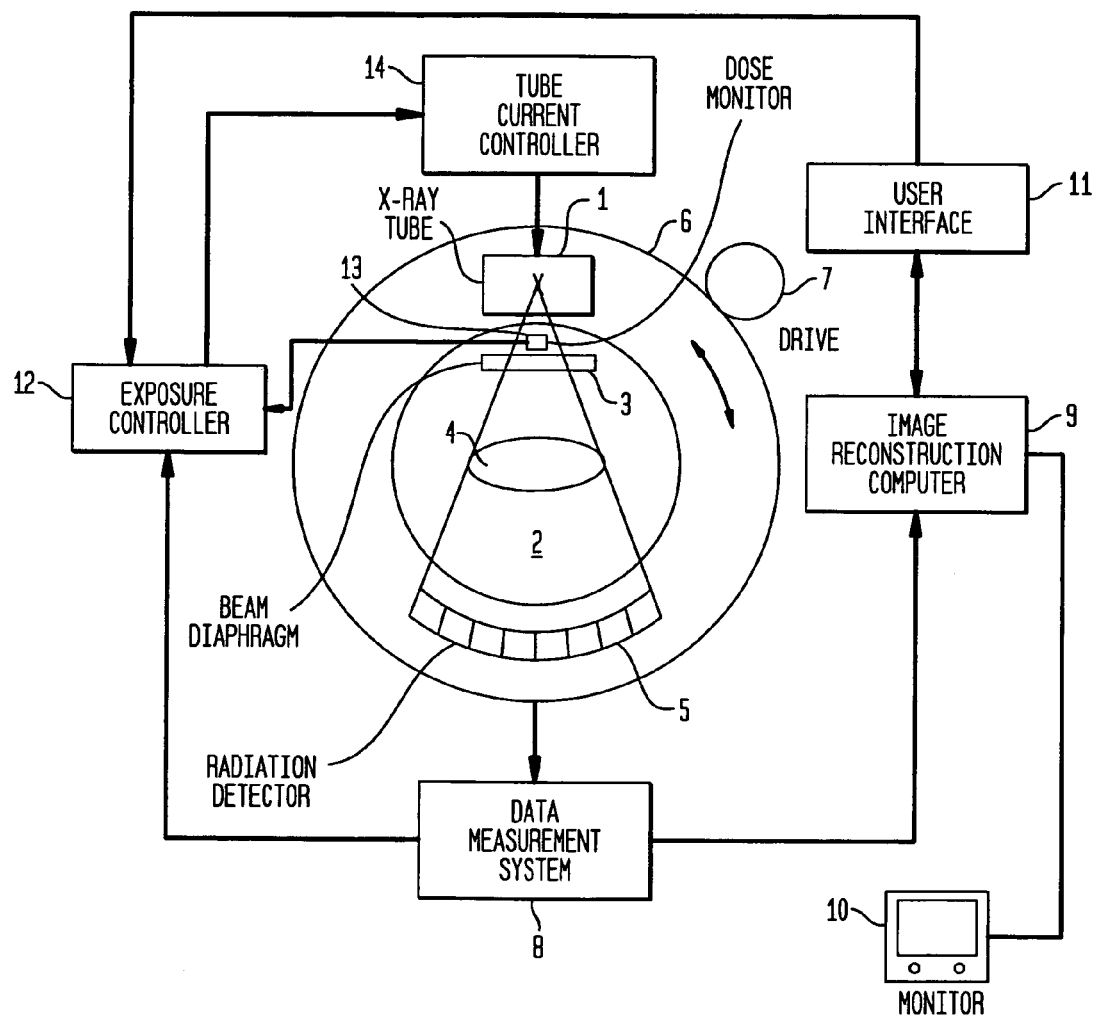
FIG. 1 is a schematic block diagram of a conventional CT apparatus.

The present invention is directed to a system and method for automatically segmenting bones in Computed Tomography Angiography (CTA) data. FIG. 1 illustrates a conventional CT system with which the present invention can be practiced. The CT system includes an X-ray tube 1 which emits an X-ray beam 2 from a focus. The X-ray beam 2 is gated by a beam diaphragm 3, and proceeds through an examination subject 4, so as to be incident on a radiation detector 5. The X-rays incident on the radiation detector 5 are attenuated by the examination subject 4, and the radiation detector 5 generates electrical signals corresponding to the attenuated X-ray incident thereon.

The X-ray tube 1 and the radiation detector 5 are mounted on a rotatable gantry 6, which is rotated by a drive 7. The X-ray beam 2 is therefore caused to rotate around the examination subject 4, so that a series of projections, respectively obtained at different projection angles, are made. Each projection has a dataset of the aforementioned electrical signals associated therewith. These datasets are supplied from the radiation detector 5, for each projection, to a data measurement system 8 for collection and editing, and the datasets are supplied from the data measurement system 8 to an image reconstruction computer 9, which constructs a CT image of the examination subject 4 from the projection data in a known manner. This image is displayed on a monitor 10 connected to the computer 9.

The system also includes a user interface 11 which is connected to the image reconstruction computer 9. The image reconstruction computer 9 also serves as the system control computer and includes connections in a known manner (not shown) to various components such as drive 7, a voltage supply for the X-ray tube 1, embodied in a tube current controller 14, and the beam diaphragm 3. Alternatively, a separate control computer can be used for this purpose.

The system may also include an exposure controller 12 and a dose monitor 12. The exposure controller 12 receives a signal from the dose monitor 13, which is disposed in the X-ray beam 2, indicating the intensity of the X-rays before being attenuated by the examination subject 4. The exposure controller 12, also receives signals from the data measurement system 8, representing the attenuated X-rays, so that the exposure controller 12 can calculate an attenuation profile of the patient 4 from the signals from the dose monitor 13 and the data measurement system 8.

Figure 2:
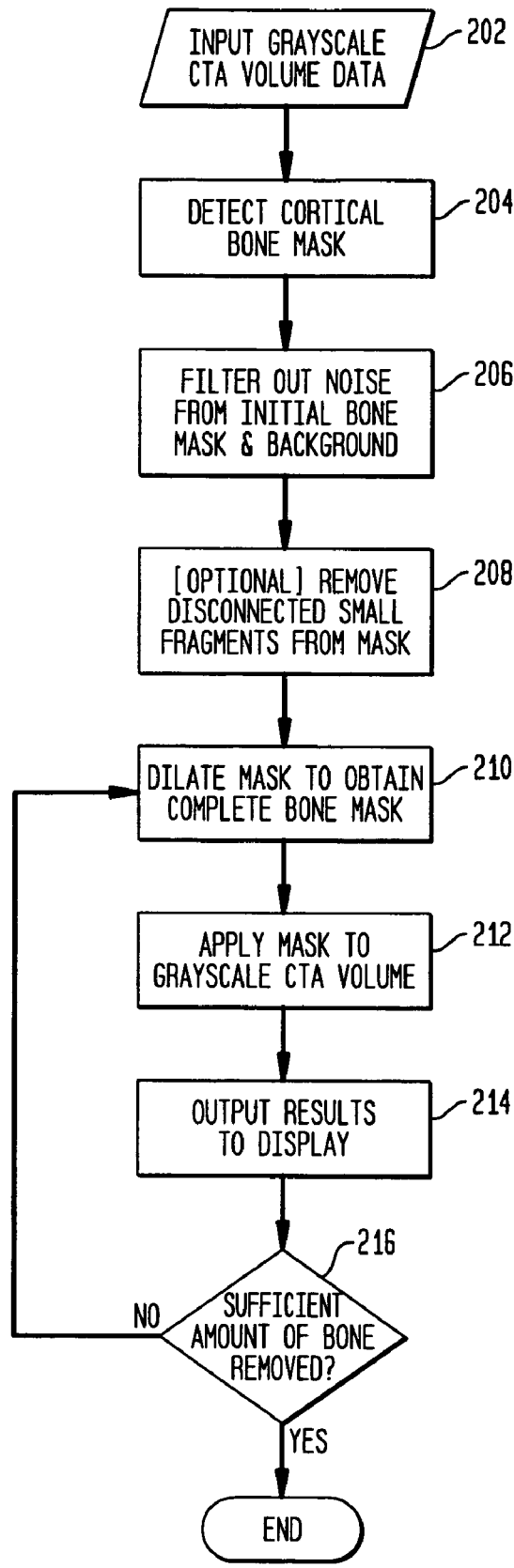
FIG. 2 is a flow chart depicting overall workflow of an automatic bone mask extraction method integrated into a visualization framework in accordance with the present invention.

FIG. 2 is a flow chart depicting the steps for automatically segmenting bone masks from CTA image volume data in accordance with the present invention. The method described hereinafter is automatic in that no initial spatial input is required from the user for identifying bone regions. The image reconstruction computer 9 of FIG. 1 receives input grayscale CTA volume data (step 202). An initial bone region is automatically generated by specifically detecting a cortical bone mask (step 204). Noise is filtered from the initial bone mask as well as the image background (step 206). Next, an optional step can be performed to remove disconnected small fragments from the bone mask (step 208). The fragment removal step can be used to reject any disconnected undefined objects such as stents in the vessels which may be falsely included from the detection. The cortical bone region is then dilated to adjacent trabecular bones to obtain a final bone segmentation (step 210).

The bone mask is then applied to a grayscale CTA volume (step 212). Results of the application are outputted to display 10 (step 214). A check is then made to determine if a sufficient amount of bone has been removed (step 216). If so, the method is complete. If not, dilation of the bone mask is again performed and steps 210-214 are repeated as necessary.

An important requirement for a successful detector for performing the inputting of the grayscale CTA volume data (step 202) is the ability to detect bone regions without misclassification of contrast enhanced vessels as bones. The detector of the present invention introduces a novel approach for distinguishing bones from contrast enhanced vessels in similar intensity ranges by utilizing local gradient vector information. By using the detector of the present invention, even when only observing in a small local region, cortical bone is distinguishable from a contrast enhanced vessel since the vessels are fairly homogeneous in intensity, whereas bones are composed of brighter cortical bones surrounded by dimmer trabecular bones and soft tissues. This observation is detectable through the comparisons of local gradients.

Figure 3A:
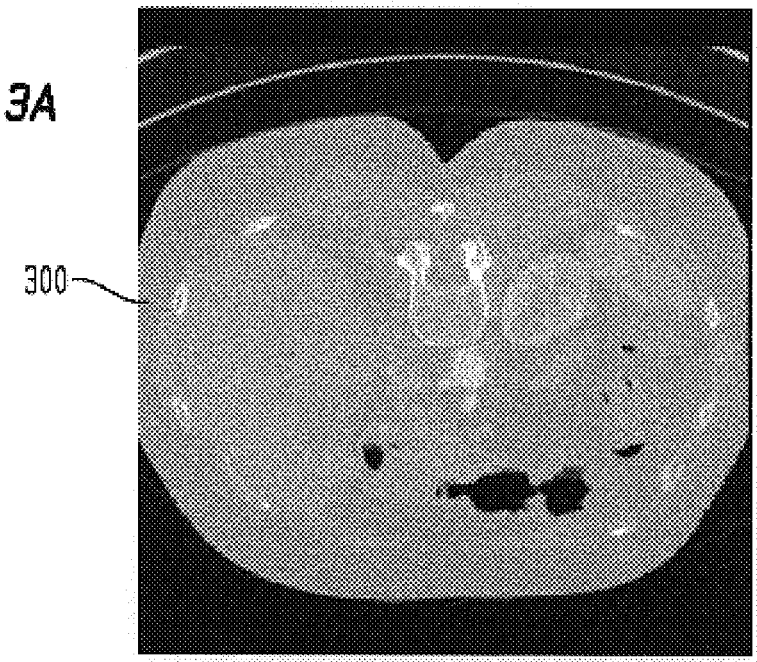
FIGS. 3a and 3b are a sample CTA slice showing the cross section of spine and rib bones as well as large vessels in accordance with the present invention.
Figure 3B:
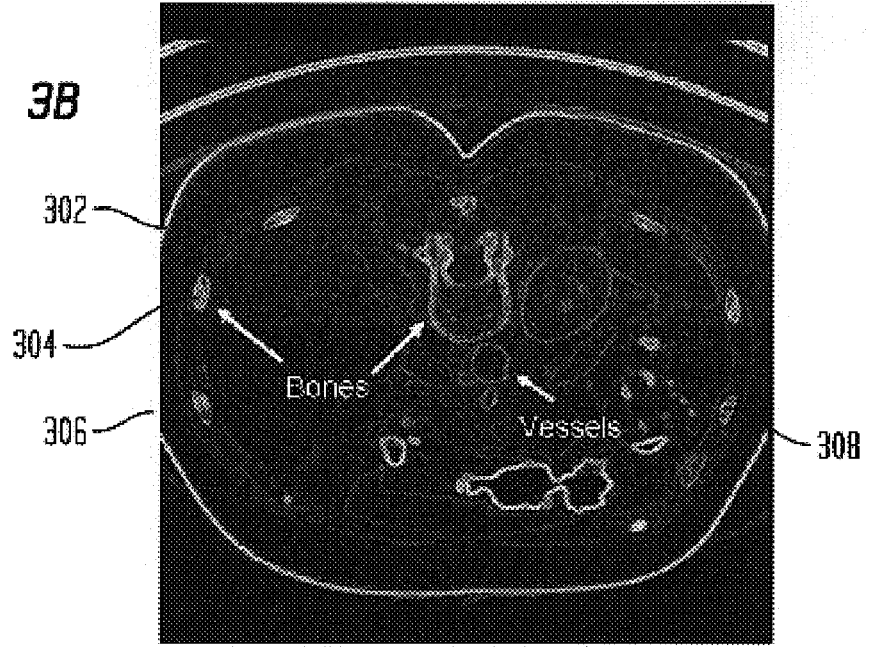

FIG. 3a illustrates a sample CTA image slice 300 showing the cross section of spine and rib bones as well as large vessels. FIG. 3b illustrates the corresponding gradient magnitude image showing the characteristic double line pattern around the spine and rib cortical bones but absent around the vessels. For example, FIG. 3b illustrates the result of observing the gradient magnitude of a typical spine in a 2D CTA image 302 and that of a contrast enhanced vessel; similar characteristics are found in 3D images. A characteristic double line 304, 306 surrounding the spine cortical bones formed by high gradient magnitude regions is shown, whereas only a single high gradient magnitude line 308 outlines the border of the vessel.

Figure 4A:
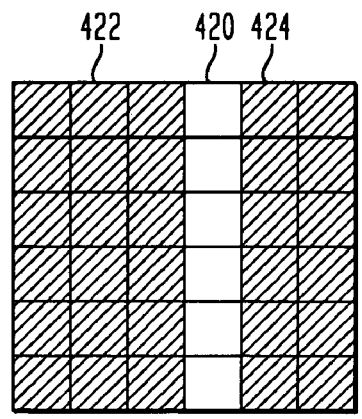
FIGS. 4a-4c are simplified 2D cortical bone ridge patterns in accordance with the present invention.
Figure 4B:
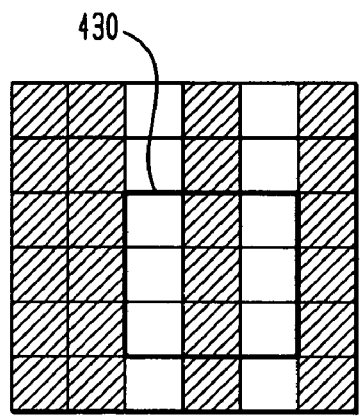
Figure 4C:
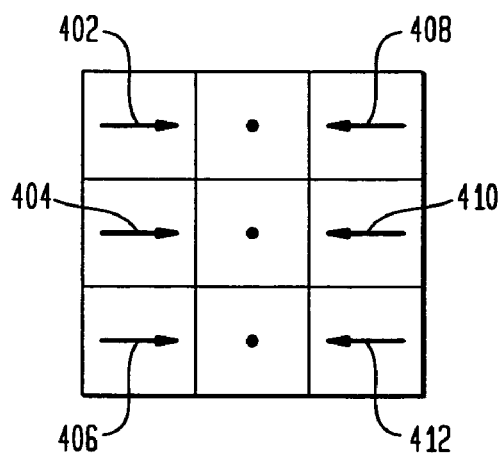

The double pattern line is expressed in the local gradient vectors as shown as a simplified 2D pattern in FIGS. 4a-4c. FIG. 4a illustrates a simplified 2D cortical bone ridge pattern. White region 420 indicates cortical bone region surrounded by darker spongy bone and soft tissues 422, 424. FIG. 4b illustrates the corresponding gradient magnitude map including a characteristic double bright lines pattern 430. FIG. 4c illustrates the pattern of the gradient vectors 402-412 surrounding a local 3×3 region centered on the cortical ridge.

That is, the gradient vectors surrounding voxel on the cortical bone ridge are pointed in opposing directions with respect to each other as represented by arrows 402-412. The detection of this condition can be done by checking that $\gamma > \tau$, where $\tau$ is a threshold selected based on the targeted data intensity and $\gamma$ is defined, for example, in the case for detecting ridges that are orientated perpendicular to the x direction surrounding a voxel located at $(x,y,z)$ with intensity $f(x,y,z)$ as follows:

$$\gamma = |\nabla f(x+r,y,z)| + |\nabla f(x-r,y,z)| - |\nabla f(x+r,y,z) + \nabla f(x-r,y,z)| \quad (1)$$

The parameter r determines the resolution at which the ridge is to be detected. This can be increased for wide ridges and decreased for detecting thin ridges. Detection of ridges in different orientations is done by computing $\gamma$ along different directions. To prevent the misclassification of points to be ridges, the number of orientations that satisfy this condition is limited for final detection.

The detection method of the present invention is more robust than other methods such as thresholding for extracting thin cortical bones where the cortical bone intensity can be low and highly variable. For speed performance efficiency, the detection can be restricted to only voxels within a predefined threshold range that exclude soft tissues. However, unlike methods such as thresholding where small errors in the selection of the threshold range may result in significant error such as the inclusion of contrast enhanced vessels, the threshold range selected for the above mentioned detector can be liberally selected without significantly affecting the results, thus providing robustness and ease of use across various data.

The local processing nature of the detector also greatly benefits its speed and memory efficiency. This is particularly suitable for processing large datasets. With each voxel processed only once, this method naturally yields to an implementation that accesses the data memory sequentially without duplicating memory paging. In addition, different regions of the volume can be processed in multiple threads on different CPUs for accelerated speed without conflicts in data access.

Small noise in the data usually does not affect the cortical bone detection results significantly since the selection of $\tau$ can rule out small detection noises. In the case where noise and areas of the thin bone may have similar level of gradient differences, additional filtering may be desirable. One option for filtering is to apply a noise filter such as a median filter to the volume image data before applying the detector. This had shown to be effective, although it undesirably requires significant additional memory and processing time for large datasets. It is more practical to apply a noise filter to the detected initial cortical bone labeled volume, typically stored as a small binary volume.

In a typical detected initial cortical bone binary volume, noise can exhibit in two forms. First, noise can appear as small detected grains in non-bone regions. Second, noise can appear as small holes in the detected bone regions. It is required that both of these types of noises are removed without significantly changing the overall shape and connectivity of the binary volume. These requirements are not satisfied by traditional binary morphological filters such as the opening and closing operators, which can result in lost of detected thin bone regions or significantly change the overall shape by smoothing and joining of disconnected regions.

Figure 5A:
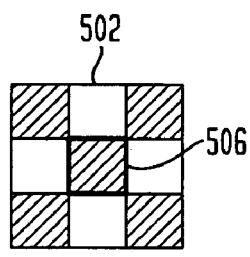
FIGS. 5a and 5b illustrate the structure elements used in filtering of noise in the detected initial binary cortical bone volume in accordance with the present invention.
Figure 5B:
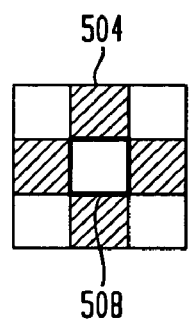

A binary volume (and image) filter is designed to satisfy the above mentioned filtering requirements in this invention. In fact, both types of noise can be addressed simultaneously without significant loss of shape by using two checkerboard structure elements as shown in FIGS. 5a and 5b to detect the relative amount of isolated noise specks in the foreground (bone) and background (non-bone) regions. The structure elements 502, 504 (as shown for the 2D case) are used in the filtering of noise in the detected initial binary cortical bone volume. The bold outlines 506, 508 indicate the origin of the structure elements. The new filtered value using this approach is computed as described below.

Let f(x,y,z) represent the values of the initial binary volume around (x,y,z) within a defined region, i.e. f(x,y,z)=0 or 1 at any one voxel within this region. The structure elements A and B used are as shown in FIGS. 5a and 5b. The new filtered values are computed as:

$$f'(x,y,z)=1 \text{ if } \alpha(x,y,z)-\beta(x,y,z) > \epsilon_1 \quad (2)$$

$$f'(x,y,z)=0 \text{ if } \beta(x,y,z)-\alpha(x,y,z) > \epsilon_2 \quad (3)$$

where $\alpha(x,y,z)$ is the number of values in $A \cup F$ when A has its origin at (x,y,z)

$\beta(x,y,z)$ is the number of values in $B \cup F^c$ when B has its origin at (x,y,z)

$$F=\{(x,y,z)\backslash f(x,y,z)=1\}$$

$$F^c=\{(x,y,z)\backslash f(x,y,z)=0\}$$

$\epsilon_1$ and $\epsilon_2$ are user chosen positive integer values. Typically, the region around (x,y,z) defined for f(x,y,z) is chosen as the same size region as the structure elements.

The resulting behavior of this computation is such that in background regions with disconnected noise specks, the expression $\beta(x,y,z)-\alpha(x,y,z)$ becomes positive and the region is set to zero when this difference is above the given threshold. Conversely, the expression $\alpha(x,y,z)-\beta(x,y,z)$ becomes positive in regions of the detected initial bone mask is mostly non-zero except for some isolated holes in the detection. In this case, the region is set to one to remove holes in the densely detected bone region. It is apparent then, that this filter is able to remove isolated noise specks as well as reinforce the detection results with just one pass through the binary detected volume. This again, leads to a memory efficient implementation that favors usage for large datasets. Furthermore, this filter can be optionally applied in a multi-resolution, iterative fashion to capture noise grains at different sizes.

In the final step of the bone segmentation workflow (FIG. 2), a dilation step is done to the filtered cortical bone volume to incrementally expand the mask to adjacent trabecular bone regions. The dilation can be applied iteratively with a constraint that the region should be within a threshold range in the original CTA volume to retain the authenticity of the bone shape while capturing as much trabecular bones as possible.

Figure 6:
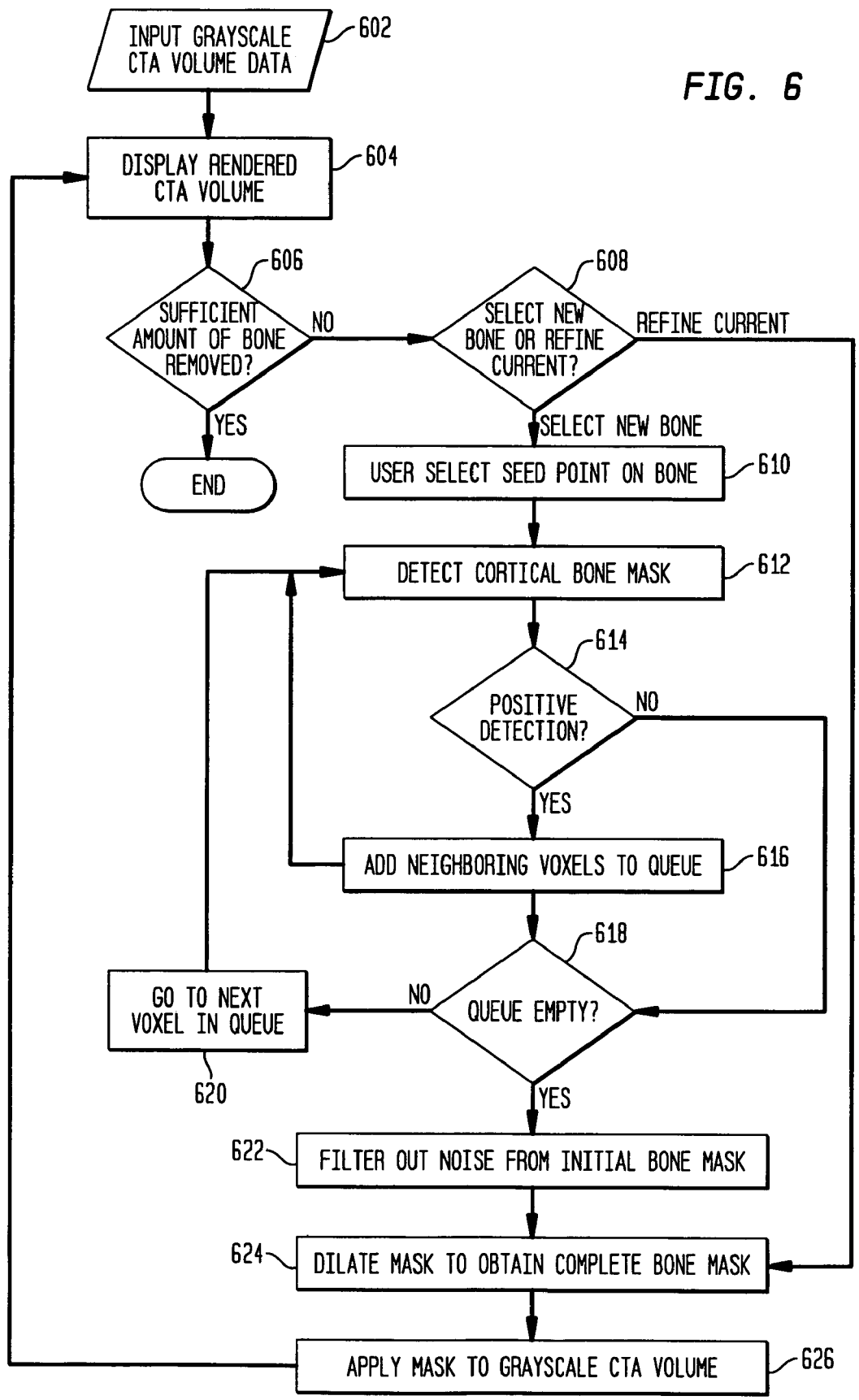
FIG. 6 is a flowchart depicting bone mask extraction interactions and processing steps as adapted to a semi-automatic workflow that requires user provided seed points in accordance with the present invention.

In accordance with an alternative embodiment of the present invention, a semi-automatic method for bone mask extraction may be employed in which the user may provide a seed point on a bone to initialize the detection step. This method, as integrated in a visualization feedback framework, is illustrated in FIG. 6. In this method, rather than processing all voxels in a sequential manner, the bone detection starts at a user provided voxel seed point location. If the detection is positive, neighboring voxels are added to the detection processing queue. Each voxel in the queue is processed through the bone detector until the queue is exhausted.

Grayscale CTA volume data is inputted to image reconstruction computer 9 (FIG. 1) (step 602). The rendered CTA volume data is displayed on monitor 10 (step 604). A determination is made as to whether a sufficient amount of bone has been removed (step 606). If a sufficient amount of bone has been removed, the process is complete. If a sufficient amount of bone has not been removed, a determination is made as to whether a new bone region is to be added or if current bone mask needs to be refined (step 608). If the current bone mask needs to be refined, the bone mask is dilated to obtain complete bone mask (step 622) and the bone mask is applied to the grayscale CTA volume data (step 624, 626).

If a new bone region is to be added, a user selects a new seed point on the cortical bone region in the CTA data (step 610). The cortical bone detector is applied to the seed point (step 612). A determination is made as to whether it is a positive detection (step 614). If it is a positive detection, neighboring voxels are added to the queue (step 616) and step 612 is repeated. Next a determination is made as to whether the queue is empty (step 618). If a positive detection is not made in step 614, the process proceeds to step 618. If the queue is not empty, the next voxel in the queue is retrieved (step 620) and the method returns to step 612.

If the queue is empty, noise from the initial bone mask is filtered out (step 622). The bone mask is then dilated to obtain a complete bone mask (step 624). The bone mask is applied to the grayscale CTA volume data (step 626) and the newly rendered CTA volume data is displayed (step 604).

The semi-automatic detection method traverses the volume similar to region growing based methods and has a disadvantage that the data memory is no longer accessed sequentially. Acceleration methods such as symmetric processing techniques can also no longer be applied. On the other hand, in cases where foreign objects such as vessel stents are present in the data, the automatic workflow may sometimes falsely detect these undefined objects as bones if they happen to have similar image properties as bones. In these cases, a fragment removal step to remove these disconnected objects may be added in the automatic extraction workflow. This extra step is not necessary in the semi-automatic case since disconnected objects are not traversed. Also, evaluation of the $\beta(x,y,z)-\alpha(x,y,z)$ term in the filtering step is not required since the background had already been excluded from traversal based on region connectivity. The elimination of these steps in the semi-automatic workflow can sometimes compensate for its disadvantage in random memory access, making its overall speed performance comparable to the automatic workflow.

The alternative semi-automatic workflow is sometimes preferred by some user due to its intuitive user interface and perceptually predictable outcome. In these cases, this semi-automatic adaptation of the bone extraction method is still more robust than other region growing and threshold constraint based method since connected contrast enhanced vessels are not falsely included in the results due to the unique gradient vector feature considered by the bone detector described in this invention.

Having described embodiments for a method for automatic bone mask extraction from CTA data, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

I claim:

1. A method for segmenting bone regions from Computed Tomography Angiography (CTA) volume data comprising the steps of:
    receiving grayscale CTA volume data, said CTA volume data containing bone regions and contrast agent filled vessels;
    automatically detecting and distinguishing between bone regions and contrast agent filled vessels in the CTA volume data;
    filtering noise from detected bone regions; and
    dilating the filtered detected bone regions to adjacent bones,
    wherein bone regions are detected by computing the following formula:
    $\gamma = |\nabla f(x+r,y,z)| + |\nabla f(x-r,y,z)| - |\nabla f(x+r,y,z) + \nabla f(x-r,y,z)|$,
    where $f(x,y,z)$ is an intensity at spatial coordinate $(x,y,z)$ and r is a resolution at which the bone regions are to be detected, and
    wherein a value of $\gamma > \tau$ is identified as an initial bone region prior to filtering and dilating, where $\tau$ is a targeted threshold value.

2. The method of claim 1 further comprising the step of: removing disconnected regions from the CTA volume data.

3. The method of claim 1 wherein the detecting step is performed by a locally operated bone detector that utilizes gradient vectors around a voxel for distinguishing bone regions from vessels with similar CTA volume data value intensities.

4. The method of claim 1 further comprising the steps of:
    applying the dilated detected bone region to the received grayscale CTA volume data; and
    displaying the applied CTA volume data.

5. The method of claim 3 wherein the locally operated bone detector uses symmetric processing techniques on multiple threads and central processing units.

6. The method of claim 1 wherein the filtering step is performed using checkerboard structure elements for matching noise grain patterns to determine a type of filtering action.

7. A system for automatically segmenting bone regions from Computed Tomography Angiography (CTA) volume data comprising:
    a locally operated bone detector for distinguishing between bone regions and contrast agent filled vessels;
    a filtering operator for removing noise from the detected bone regions;
    a dilator for expanding the filtered detected bone regions to adjacent trabecular bones;
    a processor for applying the dilated detected bone regions to the CTA volume data; and
    a display for displaying the applied CTA volume data,
    wherein the bone regions are detected by computing the following formula:
    $\gamma = |\nabla f(x+r,y,z)| + |\nabla f(x-r,y,z)| - |\nabla f(x+r,y,z) + \nabla f(x-r,y,z)|$,
    where $f(x,y,z)$ is an intensity at spatial coordinate $(x,y,z)$ and r is a resolution at which the bone regions are to be detected, and
    wherein a value of $\gamma > \tau$ is identified as an initial bone region prior to filtering and dilating, where $\tau$ is a targeted threshold value.

8. The system of claim 7 wherein the locally operated bone detector utilizes adjacent gradient vectors around a voxel for distinguishing bone regions from vessels with similar intensities.

9. The system of claim 7 wherein the locally operated bone detector utilizes symmetric processing techniques on multiple threads and central processing units.

10. The system of claim 7 wherein the filtering operator utilizes checkerboard structure elements for matching noise grain patterns to determine a type of filtering action.

11. The method of claim 1, wherein the filtering step further comprises simultaneously removing noise grains from a background and a foreground of a detected bone region.

12. The system of claim 7, wherein the filtering operator simultaneously removes noise grains from a background and a foreground of a detected bone region.

* * * * *